(12) United States Patent
Dueppenbecker et al.

(10) Patent No.: US 10,874,366 B2
(45) Date of Patent: Dec. 29, 2020

(54) MAMMOGRAPHY IMAGING

(71) Applicant: Siemens Healthcare GmbH, Erlangen (DE)

(72) Inventors: Peter Michael Dueppenbecker, Herzogenaurach (DE); Marcus Radicke, Veitsbronn (DE); Oliver Schmidt, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 93 days.

(21) Appl. No.: 16/214,189

(22) Filed: Dec. 10, 2018

(65) Prior Publication Data
US 2019/0175129 A1 Jun. 13, 2019

(30) Foreign Application Priority Data
Dec. 12, 2017 (EP) .................................... 17206758

(51) Int. Cl.
*A61B 6/00* (2006.01)
*A61B 6/04* (2006.01)
(Continued)

(52) U.S. Cl.
CPC .............. *A61B 6/502* (2013.01); *A61B 6/025* (2013.01); *A61B 6/0414* (2013.01);
(Continued)

(58) Field of Classification Search
None
See application file for complete search history.

(56) References Cited

U.S. PATENT DOCUMENTS

| 5,664,573 A | 9/1997 | Shmulewitz |
| 2003/0149364 A1 | 8/2003 | Kapur et al. |

(Continued)

FOREIGN PATENT DOCUMENTS

| CN | 101278863 A | 10/2008 |
| CN | 104349721 A | 2/2015 |

(Continued)

OTHER PUBLICATIONS

European Search Report for European Application No. EP17206758 dated Jun. 12, 2018.

(Continued)

*Primary Examiner* — Katherine L Fernandez
*Assistant Examiner* — Yi-Shan Yang
(74) *Attorney, Agent, or Firm* — Harness, Dickey & Pierce, P.L.C.

(57) ABSTRACT

A mammography installation includes a first compression device; a second compression device including an integrated X-ray detector; an X-ray emitter; a support device, arranged at the first compression device or at the second compression device, and including an integrated ultrasound transducer, the support device and the integrated ultrasound transducer being designed to be deformable so as to be adaptable to the breast of a patient, the integrated ultrasound transducer being arranged on an elastic substrate; and a breast locating region, provided between the support device and the first compression device or the second compression device that is situated opposite the first compression device or the second compression device at which the support device is arranged. The breast of the patient is positionable in the breast locating region. Further, the integrated ultrasound transducer is oriented in a direction of the breast locating region.

16 Claims, 8 Drawing Sheets

(51) Int. Cl.
  *A61B 8/08* (2006.01)
  *A61B 8/00* (2006.01)
  *A61B 6/02* (2006.01)
  *A61B 5/00* (2006.01)

(52) U.S. Cl.
  CPC .......... *A61B 6/0435* (2013.01); *A61B 8/0825* (2013.01); *A61B 8/4416* (2013.01); *A61B 8/5261* (2013.01); *A61B 5/0091* (2013.01); *A61B 5/4312* (2013.01); *A61B 6/4417* (2013.01); *A61B 6/4441* (2013.01); *A61B 6/5247* (2013.01); *A61B 6/542* (2013.01); *A61B 8/4281* (2013.01); *A61B 8/4477* (2013.01); *A61B 8/58* (2013.01)

(56) References Cited

U.S. PATENT DOCUMENTS

| | | | |
|---|---|---|---|
| 2008/0242979 A1 | 10/2008 | Fisher | |
| 2008/0249415 A1 | 10/2008 | Okamura et al. | |
| 2011/0087098 A1 | 4/2011 | Fischer et al. | |
| 2013/0107487 A1* | 5/2013 | Wodnicki | H05K 1/144 361/784 |
| 2014/0180082 A1* | 6/2014 | Evans | A61B 8/0825 600/427 |
| 2015/0139518 A1 | 5/2015 | Oohashi et al. | |
| 2015/0165479 A1 | 6/2015 | Lasiter et al. | |
| 2015/0196276 A1* | 7/2015 | Seo | B06B 1/0292 600/459 |
| 2016/0166234 A1 | 6/2016 | Zhang et al. | |
| 2017/0367656 A1* | 12/2017 | Ohishi | A61B 8/40 |
| 2018/0184999 A1* | 7/2018 | Davis | A61B 6/0414 |

FOREIGN PATENT DOCUMENTS

| | | |
|---|---|---|
| CN | 105193447 A | 12/2015 |
| DE | 10255856 A1 | 8/2003 |
| DE | 102008009967 A1 | 9/2009 |
| DE | 102013219252 A1 | 3/2015 |
| DE | 102015218607 A1 | 3/2017 |
| EP | 3372168 A1 | 9/2018 |
| JP | 2008173291 A * | 7/2008 |
| JP | 2008173291 A | 7/2008 |
| WO | WO 2015089453 A1 | 6/2015 |

OTHER PUBLICATIONS

Extended European Search Report and English translation thereof dated Jul. 12, 2018.
European Intention to Grant and English translation thereof dated Nov. 7, 2019.

* cited by examiner 13, 13.M, 16

MAMMOGRAPHY IMAGING

PRIORITY STATEMENT

The present application hereby claims priority under 35 U.S.C. § 119 to European patent application number EP17206758.9 filed Dec. 12, 2017, the entire contents of which are hereby incorporated herein by reference.

FIELD

Embodiments of the invention generally relate to a mammography installation for radiographic and ultrasonic imaging of a breast of a patient, and to a method for providing a radiographic image data record and an ultrasonic image data record of the breast of the patient.

BACKGROUND

Under normal circumstances, for the purpose of screening and diagnosis of breast cancer, use is primarily made of an X-ray mammography installation by which radiographic imaging of a breast of a patient is carried out. Young women in particular have a high proportion of dense breast tissue. During the radiographic imaging, the dense breast tissue absorbs X-radiation in a manner which is to some extent similar to potential tumor tissue, making it difficult to distinguish between dense breast tissue and potential tumor tissue.

Therefore additional ultrasonic imaging of the breast is preferably recommended for a patient with dense breast tissue. In particular, the complementary contrast of the ultrasonic imaging to the X-ray absorption can allow a reliable diagnosis. The ultrasonic imaging in this case can for example be carried out either manually using a conventional ultrasound probe or via an automatic breast volume scanner. The manual imaging is usually relatively time-intensive and in particular requires an experienced doctor or sonographer. The automatic breast volume scanner typically has a linear ultrasound transducer and a mechanical traversing unit, whereby the ultrasonic imaging of the breast of the patient can be carried out automatically, in particular without intervention by the doctor. Such an examination of the breast can nonetheless last up to 20 minutes. Two separate appointments are therefore usually made for the radiographic imaging and the ultrasonic imaging.

Whereas the radiographic imaging of the compressed breast is typically carried out while the patient is in a standing position, the patient is usually lying down in the case of ultrasonic imaging, during which the breast is typically compressed only slightly or not at all. Therefore a radiographic image data record of the radiographic imaging and an ultrasonic image data record of the ultrasonic imaging are usually difficult for a radiographer to evaluate in parallel. Furthermore, an exact image registration of the radiographic image data record and the ultrasonic image data record is not usually possible.

DE 10 2008 009 967 A1 discloses a mammography installation for examining a breast, wherein a first base plate and a second base plate comprising an ultrasound transducer are exchanged between the radiographic examination and the ultrasonic examination.

SUMMARY

At least one embodiment of the invention specifies a mammography installation which allows radiographic and ultrasonic imaging in immediate succession.

Advantageous developments are specified in the claims.

At least one embodiment of the inventive mammography installation for radiographic and ultrasonic imaging of a breast of a patient comprises
 a first compression device,
 a second compression device,
 a support device,
 an X-ray emitter,
 an integrated X-ray detector and
 an integrated ultrasound transducer which is designed as an even layer,
 wherein the second compression device comprises the integrated X-ray detector,
 wherein the support device is arranged at the first compression device or at the second compression device and
 wherein a breast locating region is provided between the support device and the compression device that is situated opposite the compression device at which the support device is arranged, and the breast of the patient can be positioned in the breast locating region,
 wherein the support device comprises the integrated ultrasound transducer and
 wherein the integrated ultrasound transducer is oriented in the direction of the breast locating region,
characterized in that
the support device and the integrated ultrasound transducer are designed to be deformable such that they can be adapted to the breast of the patient, wherein the integrated ultrasound transducer is arranged on an elastic substrate.

At least one embodiment of the present application relates to an inventive method for providing a radiographic image data record and an ultrasonic image data record of a breast of a patient by way of a mammography installation, the method comprising:
 positioning the breast of the patient in a breast locating region of the mammography installation,
 capturing the radiographic image data record of the breast of the patient, via an X-ray emitter and an integrated X-ray detector of the mammography installation,
 capturing the ultrasonic image data record of the breast of the patient, via an evenly spread integrated ultrasound transducer of a support device of the mammography installation, wherein the support device holds the breast of the patient steady between the capturing of the image data records, and
 providing the radiographic image data record and the ultrasonic image data record.

BRIEF DESCRIPTION OF THE DRAWINGS

The invention is described and explained in greater detail below with reference to the example embodiments illustrated in the figures, in which.

DETAILED DESCRIPTION OF THE EXAMPLE EMBODIMENTS

Figure 1:
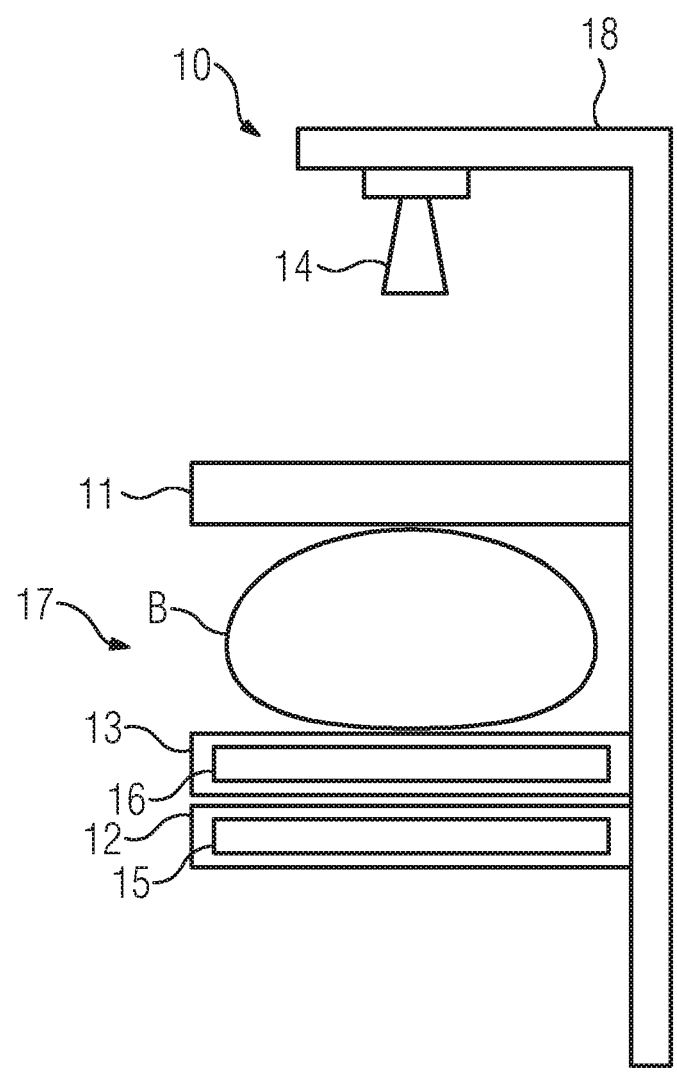
FIG. 1 shows a mammography installation in a first example embodiment.
Figure 1:
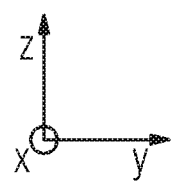

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the inventive mammography installation for radiographic and ultrasonic imaging of a breast of a patient comprises
    a first compression device,
    a second compression device,
    a support device,
    an X-ray emitter,
    an integrated X-ray detector and
    an integrated ultrasound transducer which is designed as an even layer,
    wherein the second compression device comprises the integrated X-ray detector,
    wherein the support device is arranged at the first compression device or at the second compression device and
    wherein a breast locating region is provided between the support device and the compression device that is situated opposite the compression device at which the support device is arranged, and the breast of the patient can be positioned in the breast locating region,
    wherein the support device comprises the integrated ultrasound transducer and
    wherein the integrated ultrasound transducer is oriented in the direction of the breast locating region,
characterized in that
the support device and the integrated ultrasound transducer are designed to be deformable such that they can be adapted to the breast of the patient, wherein the integrated ultrasound transducer is arranged on an elastic substrate.

In particular, the mammography installation is suitable for radiographic and ultrasonic imaging of a breast of a patient irrespective of the gender of the patient. In particular, the term patient also includes a male patient. The mammography installation typically has a stand, wherein the first compression device, the second compression device and the X-ray emitter in particular are typically connected to the stand in a mobile manner. The mammography installation can have a system axis in particular, wherein a body axis of the patient is typically oriented parallel to the system axis during the radiographic imaging and the ultrasonic imaging. The X-ray emitter, the first compression device, the second compression device, the support device and/or the integrated X-ray detector can usually be swiveled by up to 90° about a rotational axis. In particular, the rotational axis is perpendicular to the system axis of the mammography installation. For example, by swiveling the first compression device and the second compression device, the breast of the patient can be compressed from different angles, whereby the ultrasonic imaging and the radiographic imaging can capture different angles, in particular different views, of the breast of the patient. When the angle of rotation is 0° and the body axis is approximately parallel to the system axis, such imaging is referred to as craniocaudal.

The mammography installation is typically oriented for radiographic imaging and ultrasonic imaging in a standing position of the patient. In a typical application scenario, in particular when the angle of rotation is 0°, the first compression device and the second compression device are arranged one above the other vertically, such that the first compression device and the second compression device can be referred to as upper and lower compression device respectively according to their arrangement.

In particular, the X-ray emitter and the integrated X-ray detector form an X-ray system which is designed for radiographic imaging. The X-ray system typically has a radiographic control unit which controls the radiographic imaging by the X-ray system and/or is designed in particular to reconstruct a radiographic image data record in accordance with the radiographic imaging. The X-ray emitter is preferably oriented towards the integrated X-ray detector. The X-ray system typically has a ray path and a maximum field of view, wherein the ray path is typically greater than the maximum field of view and preferably encompasses the maximum field of view completely. The ray path describes in particular at least one path for X-rays starting from the X-ray emitter to the integrated X-ray detector. The maximum field of view comprises in particular a measuring region for the radiographic imaging. The first compression device is typically arranged between the X-ray emitter and the second compression device comprising the integrated X-ray detector. The X-rays are attenuated or absorbed in this case, e.g. by the first compression device and the support device comprising the integrated ultrasound transducer. The first compression device and the support device and typically the second compression device are therefore preferably designed to be particularly X-ray-transparent, thereby reducing the attenuation or absorption of the X-rays in particular.

It is conceivable in principle for the X-ray emitter to be so arranged as to be linearly mobile parallel to the first compression device and/or the second compression device. Alternatively or additionally, the X-ray emitter can be so arranged as to be mobile in a circular arc, the circular arc being defined about a rotational axis which is oriented perpendicular to the system axis of the mammography installation. In this case, it is possible to carry out e.g. three-dimensional radiographic imaging via the mammography installation, in particular radiographic tomosynthesis. In general, tomosynthesis allows a three-dimensional image to be generated from two-dimensional images which are captured from different angles of the X-ray emitter relative to the X-ray detector. The two-dimensional and/or three-dimensional images may be part of the ultrasonic or radiographic image data record.

It is typically possible to change a distance between the first compression device and the second compression device, particularly in order to compress the breast. It is conceivable in principle for one of the two compression devices to press the breast onto the other compression device. In other words, one of the two compression devices is mobile, while the other compression device is rigidly attached. The breast of the patient is typically compressed by reducing the distance between the first compression device and the second compression device. The first compression device and/or the second compression device are therefore designed to be mobile, in particular along the system axis, relative to each other and relative to the breast of the patient, i.e. in particular height-adjustable in the case of a vertical arrangement of the mammography installation. Furthermore, the first compression device and the second compression device are usually designed such that a flat side of the first compression device and of the second compression device in each case are oriented in relation to each other, in particular parallel to each other. When the breast of the patient is positioned in the breast locating region, e.g. supported on the flat side of the lower compression device, the breast is in particular compressed by adjusting the first compression device, in particular the upper compression device, and the second compression device, such that the distance between the first compression device and the second compression device changes, in particular is reduced. The first compression device and the second compression device may be designed as a compression plate in each case.

The first compression device and/or the second compression device can each have a holding device for the support device. The support device can therefore be arranged in particular in the holding device of the first compression device and/or the holding device of the second compression device. The support device is designed in particular to support and/or steady the breast. In other words, the breast is held in position by the support device in particular. The support device is arranged in particular between the first compression device and the second compression device. The compression device at which the support device is arranged is typically referred to as the compression device with support device or the supporting compression device, and the opposite compression device is referred to as the free compression device. The support device is typically so arranged as to be attached to the supporting compression device, in particular in a detachable manner. For example, the support device is securely connected to the supporting compression device during the ultrasonic imaging and the radiographic imaging, and can subsequently be removed for cleaning of the support device and then replaced again.

The integrated ultrasound transducer is designed as an even layer, i.e. in particular two-dimensional in the sense that any extent in a third dimension is preferably negligible. The integrated ultrasound transducer, in particular one side of the integrated ultrasound transducer, usually forms a broad surface, extends over a surface area and/or is flattened-out. The integrated ultrasound transducer may be designed to be flat. In other words, the integrated ultrasound transducer can have a planar state, e.g. in a starting position, wherein the integrated ultrasound transducer is not deformed in the planar state. When the integrated ultrasound transducer is adapted to the breast, the integrated ultrasound transducer typically has a deformed state. Assuming that the system axis is oriented parallel to the z-axis of the spatial coordinates, the integrated ultrasound transducer is designed as an even layer in the x-y plane in particular. It is conceivable for one side of the integrated ultrasound transducer to be designed as an even layer. The integrated ultrasound transducer can usually be designed in the form of a disk, a cuboid or a cube, wherein at least one side of the integrated ultrasound transducer is designed as an even layer in this case. For example, the even side of the integrated ultrasound transducer can have an edge length which is twice, preferably five times, particularly preferably ten times longer than an edge length of the integrated ultrasound transducer perpendicular to the even side. The integrated ultrasound transducer is preferably designed such that, in comparison with a conventional ultrasound transducer in particular, a larger surface thereof can be in contact, preferably simultaneously, with the breast of the patient. In other words, an acoustic coupling of the integrated ultrasound transducer to the breast of the patient is preferably greater than that of the conventional ultrasound transducer.

Alternatively or additionally, the integrated ultrasound transducer can be designed such that one side of the integrated ultrasound transducer extends as an even layer. The integrated ultrasound transducer has in particular a multiplicity of ultrasound transducer elements, which are preferably arranged in an evenly spread matrix. The integrated ultrasound transducer can be designed in particular to support and steady the breast. The integrated ultrasound transducer is preferably based on pMUT technology (piezoelectric micromachined ultrasound transducer). In particular, pMUT technology allows the evenly spread integrated ultrasound transducer to be produced at preferably low cost. A further advantage of the integrated ultrasound transducer based on pMUT technology is that construction of the ultrasound transducer elements typically involves the selection of materials which are at least partially X-ray-transparent. In comparison with cMUT technology (capacitive micro-fabricated ultrasound transducer) and PZT technology (piezo zirconate titanate) in particular, pMUT technology has greater X-ray-transparency. In other words, the integrated ultrasound transducer is preferably designed to be X-ray-transparent. The X-ray-transparency is advantageous in particular because the integrated ultrasound transducer can then remain in the ray path of the X-ray system during the radiographic imaging. Using a typical X-ray energy of 28 keV for the radiographic imaging, the X-ray-transparency of the integrated ultrasound transducer is at least 30%, preferably more than 50% or particularly preferably more than 80%. The X-ray energy describes in particular a maximum X-ray energy of the X-rays leaving the X-ray emitter and is predetermined and/or regulated by the radiographic control unit. In other words, assuming the typical X-ray energy of 28 keV and the 30% X-ray-transparency, approximately 30% of all X-rays pass through the integrated ultrasound transducer, for example.

The integrated ultrasound transducer is in particular part of an ultrasound system which can have an ultrasonic control unit, wherein the ultrasonic control unit in particular controls the ultrasonic imaging and/or is designed in particular to reconstruct an ultrasonic image data record in accordance with the ultrasonic imaging. Alternatively or additionally, the mammography installation can have a control unit, wherein the control unit of the mammography installation comprises the radiographic control unit and the ultrasonic control unit. The ultrasonic control unit preferably specifies an ultrasonic measuring sequence and a frequency of ultrasound waves to be emitted from the integrated ultrasound transducer according to the ultrasonic measuring sequence. The frequency of the ultrasound waves typically defines a maximum field of view of the integrated ultrasound transducer, in particular a maximum penetration depth of the ultrasound waves, wherein the maximum field of view comprises in particular a measuring region of the ultrasonic imaging. The measuring region of the ultrasonic imaging is therefore largely predetermined by a geometric size of the evenly formed side of the integrated ultrasound transducer and the frequency of the ultrasound waves. An overlap of the measuring region for the ultrasonic imaging and of the measuring region for the radiographic imaging is preferably not equal to zero. In particular, the overlap is greater than any region of the measuring region for the ultrasonic imaging and/or of the measuring region for the radiographic imaging which lies outside the overlap. The overlap between the measuring region for the ultrasonic imaging and the measuring region for the radiographic imaging is usually more than 20%, preferably more than 50% or particularly preferably at least 80%. The measuring region for the ultrasonic imaging or the measuring region for the radiographic imaging preferably encompasses the respective other measuring region completely. In other words, the measuring region for the ultrasonic imaging or the measuring region for the radiographic imaging is preferably a complete section of the other measuring region. In particularly preferred embodiment, the measuring region for the ultrasonic imaging and the measuring region for the radiographic imaging are congruent.

In particular, the integrated ultrasound transducer emits the ultrasound waves in the direction of the breast locating region, whereby the ultrasonic imaging in the breast locating region is made possible. In particular, the ultrasonic imaging of the breast of the patient is therefore possible when the breast of the patient is positioned in the breast locating region in such a way as to effect the acoustic coupling between the integrated ultrasound transducer and the breast of the patient. The acoustic coupling can be increased by using an ultrasound gel and/or by compression of the breast, for example. The integrated ultrasound transducer is typically also designed to receive the ultrasound waves. It is also conceivable in principle for the integrated ultrasound transducer to be designed to only send or receive the ultrasound waves. By way of the ultrasonic control unit, it is preferably possible to switch between sending or receiving and sending and receiving.

The breast locating region is typically provided between the support device and the free compression device. The breast locating region comprises in particular an extent between the support device and the free compression device along the system axis. In other words, the breast locating region is typically predetermined by the distance between the first compression device and the second compression device, wherein in particular an extent of the support device along the system axis is subtracted from this distance. The breast locating region preferably allows the positioning of the breast of the patient, in particular in the measuring region for the ultrasonic imaging and/or in the measuring region for the radiographic imaging. In this way, the breast of the patient can be positioned between the support device and the free compression device. An overlap of the breast locating region, the measuring region for the ultrasonic imaging and the measuring region for the radiographic imaging is typically not equal to zero. In each case, a section of the breast locating region, the measuring region for the ultrasonic imaging and the measuring region for the radiographic imaging is usually contained in the other regions respectively. Particularly preferably, the breast locating region is completely contained in the measuring region for the ultrasonic imaging and in the measuring region for the radiographic imaging.

A particular advantage of the mammography installation is that the integrated ultrasound transducer can remain in the ray path of the X-ray system during the radiographic imaging. In other words, the integrated ultrasound transducer is preferably designed such that the radiographic imaging is possible although the integrated ultrasound transducer is arranged between the X-ray emitter and the X-ray detector. An X-ray-transparent embodiment of the integrated ultrasound transducer is particularly advantageous. It is usually a further advantage that, as a result of the evenly spread form of the integrated ultrasound transducer, the measuring region for the ultrasonic imaging covers up to 70% of that region of the breast of the patient which is relevant for the diagnosis. No mechanical traversing unit is typically required for the ultrasonic imaging. It is particularly advantageous that the ultrasonic imaging and the radiographic imaging can therefore take place in quasi immediate succession and in any chosen order, whereby a total duration of the ultrasonic imaging and the radiographic imaging is reduced and the compression of the breast, potentially painful for the patient, is shortened. It is further advantageous in particular that the radiographic image data record and the ultrasonic image data record are in particular congruent, i.e. they depict the same region of the breast of the patient, whereby it is typically possible to improve the diagnosis or an evaluation. In other words, image registration between the radiographic image data record and the ultrasonic image data record is possible generally, in particular exactly, and in a particularly preferred case is unnecessary.

The support device and the integrated ultrasound transducer are designed to be deformable such that they can be adapted to the breast of the patient, wherein the integrated ultrasound transducer is arranged on an elastic substrate. Technical realization of the deformable integrated ultrasound transducer is possible by way of pMUT technology in particular. The deformable integrated ultrasound transducer can usually be adapted to the breast of the patient as an even layer, whereby the acoustic coupling of the breast to the integrated ultrasound transducer is preferably improved. A possible advantage is that by virtue of the deformable design of the integrated ultrasound transducer, the measuring region for the ultrasonic imaging covers more than 70% and particularly preferably more than 95% of the region of the breast of the patient which is relevant for the diagnosis.

The ultrasound transducer elements, in particular in a deformed and in particular curved state of the integrated ultrasound transducer, rest against a surface of the breast of the patient. The integrated ultrasound transducer can therefore preferably adapt itself to the surface of the breast of the patient and/or distort the surface of the breast of the patient to a certain extent. The integrated ultrasound transducer is preferably arranged on the elastic substrate in such a way that the integrated ultrasound transducer can be adapted to the breast in all spatial directions. The ultrasound transducer can typically be curved along an axis from a pectoralis of the patient to a mamilla of the patient, and/or along an axis which runs parallel to the pectoralis of the patient, in order to replicate the shape of the breast in particular. In comparison with a non-deformable ultrasound transducer, the deformable integrated ultrasound transducer can advantageously be adapted to the concave and individual shape of the breast of the patient. It is also possible to dispense with additional ultrasound gel, particularly in a peripheral region of the breast of the patient, thereby preferably reducing the absorption of the X-rays in the ultrasound gel.

One embodiment variant provides that the support device has a membrane, wherein the integrated ultrasound transducer is arranged at the membrane. The membrane may comprise a textile, glass, film, tissue and/or gauze. It is conceivable in principle for the membrane to at least partially surround the integrated ultrasound transducer or for the integrated ultrasound transducer to be arranged within the membrane. The membrane advantageously facilitates a contact between the integrated ultrasound transducer and the breast of the patient. The membrane advantageously exhibits low attenuation for the ultrasound waves. This embodiment variant has the advantage that the support device can be preferably adapted to the breast of the patient.

An embodiment variant provides that the compression device at which the support device is arranged is designed as a frame and the support device is mounted within the frame. In particular, if the support device comprises the membrane, the membrane is preferably mounted within the frame. The support device, in particular the integrated ultrasound transducer, is preferably attached within the frame. In particular, the frame is O-shaped, U-shaped, C-shaped or rectangular with a central recess.

An embodiment variant provides that the mammography installation has a computing unit and/or processor, wherein the mammography installation is designed to determine a deformation of the integrated ultrasound transducer and the computing unit is designed to reconstruct an ultrasonic image data record in accordance with the deformation. In particular, if the control unit of the mammography installation (in particular the radiographic control unit and/or the ultrasonic control unit) is replicated in program code segments/modules, the computing unit or porcessor is preferably able to execute the program code segments/modules. It is conceivable in principle for the mammography installation to comprise an ultrasonic computing unit for the ultrasonic imaging and/or a radiographic computing unit for the radiographic imaging. The determining of the deformation is described in one of the following sections.

An embodiment variant provides that the support device has a cushion. The cushion is preferably designed as a soft pad or bolster for the breast of the patient. The cushion can typically be adapted to the breast of the patient. By virtue of its nature, the cushion usually increases the comfort of the patient during the ultrasonic imaging and the radiographic imaging.

An embodiment variant provides that the support device has a first side facing the breast locating region and a second side facing the compression device at which the support device is arranged, wherein the first side comprises the integrated ultrasound transducer. The advantage of this embodiment variant is that the integrated ultrasound transducer is preferably in direct contact with the breast of the patient, thereby providing the acoustic coupling for the ultrasonic imaging. Therefore only ultrasound gel preferably lies between the ultrasound transducer elements and the breast of the patient in this case, whereby the acoustic coupling is typically improved.

An embodiment variant provides that the second side of the support device comprises the cushion. In other words, the cushion is preferably arranged between the integrated ultrasound transducer and the supporting compression device. In this case, the integrated ultrasound transducer is therefore preferably in contact with the breast of the patient and the cushion is situated in particular between the integrated ultrasound transducer and the supporting compression device. In particular, the cushion can be an air cushion or an ultrasound cushion, because the cushion is arranged on the side which faces away from the ultrasound waves and therefore preferably does not influence the acoustic coupling. It is conceivable in principle for the integrated ultrasound transducer to be designed as part of a sleeve for the cushion. In this case, ultrasonic imaging which is adapted to the breast of the patient is preferably possible, e.g. because the integrated ultrasound transducer and/or the cushion itself is designed to be deformable.

An embodiment variant provides that the support device has a first side facing the breast locating region and a second side facing the compression device at which the support device is arranged, wherein the second side comprises the integrated ultrasound transducer. This embodiment variant differs from the previously described embodiment variant, in particular in respect of an arrangement of the integrated ultrasound transducer in relation to the support device. The advantage of this embodiment variant is that the integrated ultrasound transducer can be designed in particular to be flat, i.e. planar. In this case, e.g. the support device can be adapted to the breast of the patient.

An embodiment variant provides that the first side has the cushion. In other words, the cushion is preferably arranged between the integrated ultrasound transducer and the breast locating region. In this case, the integrated ultrasound transducer can be deformable or flat, because the cushion (e.g. an ultrasound gel cushion) is preferably designed such that the cushion in combination with the ultrasound gel provides the acoustic coupling and the cushion can preferably be adapted to the breast of the patient.

An embodiment variant provides that the mammography installation comprises a computing unit, wherein the integrated ultrasound transducer is designed to capture a deformation of the support device and the computing unit is designed to reconstruct a radiographic image data record in accordance with the deformation of the support device. The capture of the deformation of the support device may comprise in particular the capture of an extent, in particular a volume, and/or a position of the ultrasound gel cushion and/or the ultrasound gel by way of the ultrasonic imaging. It is preferably possible to determine the volume of the ultrasound gel cushion or of the ultrasound gel on the basis of the ultrasonic image data record, wherein this volume is preferably used to adapt the radiographic image data record. The adaptation of the radiographic image data record may comprise in particular a correction of the absorption of the X-rays, shown in particular in the radiographic image data record, with reference to the volume of the ultrasound gel cushion or of the ultrasound gel. It is possible in particular to capture or estimate scattered rays of the radiographic imaging and to correct the radiographic image data record in accordance with the scattered rays. It is therefore an advantage of this embodiment variant that the ultrasonic image data record can be used to improve the image quality of the radiographic image data record.

An embodiment variant provides that the mammography installation has a further ultrasound transducer in addition to the integrated ultrasound transducer, wherein the further ultrasound transducer is arranged such that the breast locating region is provided between the integrated ultrasound transducer and the further ultrasound transducer. The ultrasonic control unit is preferably designed such that the integrated ultrasound transducer can receive the ultrasound waves when the further ultrasound transducer emits the ultrasound waves or vice versa. For example, both the first compression device and the second compression device can each comprise an ultrasound transducer. In this case, e.g. a further support device can comprise the further ultrasound transducer, wherein the further ultrasound transducer is arranged between the first compression device and the second compression device. Alternatively, the further ultrasound transducer can be arranged outside the first compression device and the second compression device. It is also conceivable in principle for the further ultrasound transducer to be arranged between the second compression device and the integrated X-ray detector. The further ultrasound transducer can be more powerful and larger than the integrated ultrasound transducer and designed on the basis of PZT technology for example. In particular, these embodiment variants can enable ultrasonic transmission imaging and/or ultrasonic imaging with a higher frequency of ultrasound waves. The mammography installation is preferably so designed as to support the acoustic coupling between the integrated ultrasound transducer and the further ultrasound transducer.

At least one embodiment of the present application relates to an inventive method for providing a radiographic image data record and an ultrasonic image data record of a breast of a patient by way of a mammography installation, the method comprising:

positioning the breast of the patient in a breast locating region of the mammography installation, capturing the radiographic image data record of the breast of the patient, via an X-ray emitter and an integrated X-ray detector of the mammography installation, capturing the ultrasonic image data record of the breast of the patient, via an evenly spread integrated ultrasound transducer of a support device of the mammography installation, wherein the support device holds the breast of the patient steady between the capturing of the image data records, and providing the radiographic image data record and the ultrasonic image data record.

While the patient is in a standing position, the breast of the patient is preferably positioned in the breast locating region in such a way that the integrated ultrasound transducer preferably comes into contact with the breast evenly, in particular over a larger area, e.g. as a result of the compression via the first compression device and/or the second compression device. It is also conceivable in principle for the mammography installation to be designed for the patient in a prone position.

The radiographic image data record is preferably captured in accordance with the radiographic imaging and the ultrasonic image data record in accordance with the ultrasonic imaging, and corresponding radiographic images and ultrasonic images are reconstructed.

Between the capturing of the image data records, the support device preferably holds the breast of the patient steady, such that the respective image data records can be captured in immediate succession and in any chosen order, wherein either the radiographic image data record is captured first followed by the ultrasonic image data record or the ultrasonic image data record is captured first followed by the radiographic image data record. The steadying of the breast of the patient signifies in particular that the breast of the patient must not be repositioned or moved between the capturing of the image data records. A pause between the capturing of the image data records is preferably comparatively short, i.e. one image data record is preferably recorded immediately after the other image data record. It is conceivable in principle for the image data records to be captured without a pause, i.e. quasi simultaneously depending on a respective measurement duration.

An embodiment variant provides that the capturing of the ultrasonic image data record includes determining a deformation of the evenly spread integrated ultrasound transducer, and the determining of the deformation of the evenly spread integrated ultrasound transducer comprises the following steps:

activating at least one ultrasound transducer element of the evenly spread integrated ultrasound transducer in such a way that ultrasound waves are emitted, capturing a propagation time of the ultrasound waves via the at least one ultrasound transducer element and determining the deformation of the evenly spread integrated ultrasound transducer on the basis of the propagation time of the ultrasound waves.

The activation of the at least one ultrasound transducer element can be effected individually or in groups. It is also possible in principle to activate all ultrasound transducer elements simultaneously or in a predetermined sequence. The respective ultrasound transducer elements are preferably designed to capture the ultrasound waves and, for example, the ultrasonic control unit is designed to calculate the propagation time. The determining of the deformation may require in particular information about a distance between the ultrasound transducer elements relative to each other, preferably in the flat or planar state of the integrated ultrasound transducer, and/or information about a distance to a reference object, and/or a general condition that a complete reflection of the ultrasound waves takes place at the reference object. For example, the reference object can be the first compression device, the second compression device and/or the integrated X-ray detector, the geometry thereof being captured by way of dimensioned drawings or image recordings, for example. The determining of the deformation may be effected by way of an iterative algorithm, for example, said algorithm being adapted such that the reference object represented in the ultrasonic image data record preferably corresponds to the captured geometry. The deformation of the integrated ultrasound transducer can preferably be determined according to the adaptation of the algorithm, in particular the input parameters of the algorithm. The determining of the deformation can take place in principle during the ultrasonic imaging or as part of further ultrasonic imaging for calibrating the mammography installation.

An embodiment variant provides that the determining of the deformation of the evenly spread integrated ultrasound transducer takes place using the captured radiographic image data record. In particular, the ultrasonic control unit and/or the control unit of the mammography installation can be designed to determine the deformation of the integrated ultrasound transducer by way of a two-dimensional or three-dimensional radiographic image data record. Because the integrated ultrasound transducer is typically not 100% X-ray-transparent, the deformation of the integrated ultrasound transducer can be determined from the radiographic image data record and used for the ultrasonic imaging. Alternatively or additionally, a skin line (i.e. the surface) of the breast of the patient can be taken into consideration for the purpose of determining the deformation. The deformation of the integrated ultrasound transducer can typically be determined by way of the two-dimensional or three-dimensional radiographic imaging, in particular by way of the radiographic tomosynthesis. Alternatively or additionally, the integrated ultrasound transducer can have a number of X-ray-absorbent markings which are visible in the radiographic imaging. In this case, a planar distance X between the X-ray-based markings in the flat or planar state of the integrated ultrasound transducer is preferably known. Using the radiographic image data record, it is preferably possible to capture a deformed distance X', wherein the deformation of the integrated ultrasound transducer is determined using the planar distance X and the deformed distance X'. It is conceivable in principle for the deformation of the evenly spread integrated ultrasound transducer to be determined by using the captured radiographic image data record and capturing the propagation time of the ultrasound waves in combination.

The determining of the deformation of the integrated ultrasound transducer preferably makes the ultrasonic imaging possible and particularly preferably makes it comparatively better. A further advantage may be the possibility of improving three-dimensional ultrasonic imaging on the basis of the determined deformation of the integrated ultrasound transducer.

Alternatively or additionally, the ultrasound waves can be focused on a region according to the deformation of the integrated ultrasound transducer, whereby ultrasonic therapy may be possible via the mammography installation in addition to the ultrasonic imaging and the radiographic imaging.

An embodiment variant provides that the ultrasonic image data record is reconstructed in accordance with the deformation of the evenly spread integrated ultrasound transducer. The control unit of the mammography installation can preferably be designed such that the ultrasonic image data record can be reconstructed in accordance with the deformation of the integrated ultrasound transducer. The control unit of the mammography installation can be replicated in program code segments/modules in such a way that the computing unit or processor of the mammography installation can execute the program code segments/modules for reconstructing the ultrasonic image data record and/or the radiographic image data record. The ultrasonic image data record and/or the radiographic image data record can preferably be provided or displayed on a monitor of the mammography installation for evaluation or diagnosis. Alternatively or additionally, the ultrasonic image data record and/or the radiographic image data record can be stored on a server and retrieved subsequently, for example.

An embodiment variant provides that a deformation of the support device by the evenly spread integrated ultrasound transducer is captured and the radiographic image data record is reconstructed in accordance with the deformation of the support device. This has the advantage that the integrated ultrasound transducer is able to capture a cushion, in particular an ultrasound gel cushion, and the radiographic image data record can be adapted or corrected by way of the captured cushion. This is advantageous in particular for the purpose of correcting the absorption of the X-rays with reference to the cushion.

Functions, advantages or alternative embodiment variants cited in the description of the device can also be transferred to the method and vice versa. In other words, claims relating to the method can be developed by features of the device and vice versa. In particular, the inventive device can be used in the method.

FIG. 1 shows a mammography installation 10 for radiographic and ultrasonic imaging of a breast B of a patient in a side view of the mammography installation 10. The mammography installation 10 comprises a first compression device 11, a second compression device 12, a support device 13, an X-ray emitter 14, an integrated X-ray detector 15 and an integrated ultrasound transducer 16 which is designed as an even layer. The second compression device 12 comprises the integrated X-ray detector 15. The support device 13 in this example embodiment is arranged at the second compression device 12. A breast locating region 17 is provided between the support device 13 and the first compression device 11. The breast B of the patient is positioned in the breast locating region 17 in this case.

The support device 13 comprises the integrated ultrasound transducer 16, this being oriented in the direction of the breast locating region 17. It is conceivable in principle for the support device 13 to be permanently integrated in one of the two compression devices, i.e. the second compression device 12 in this case. The first compression device 11 and the second compression device 12 are height-adjustable in a stand 18 of the mammography installation 10 and are so arranged as to compress the breast B. The breast B of the patient is illustrated only schematically.

With reference to the system of coordinates shown in FIG. 1, a shoulder of the patient is oriented parallel to the x-axis and an axis between pectoralis and mamilla is oriented along the y-axis in this example embodiment. The body axis of the patient is parallel to the z-axis. The integrated ultrasound transducer 16 is designed as an even layer in relation to the x-y plane. In this example embodiment, the integrated ultrasound transducer 16 is designed to be flat or planar. The system axis of the mammography installation 10 corresponds to the z-axis.

In the following description of the figures, those structures and units which remain essentially the same are normally denoted by the reference signs first shown in FIG. 1.

Figure 2:
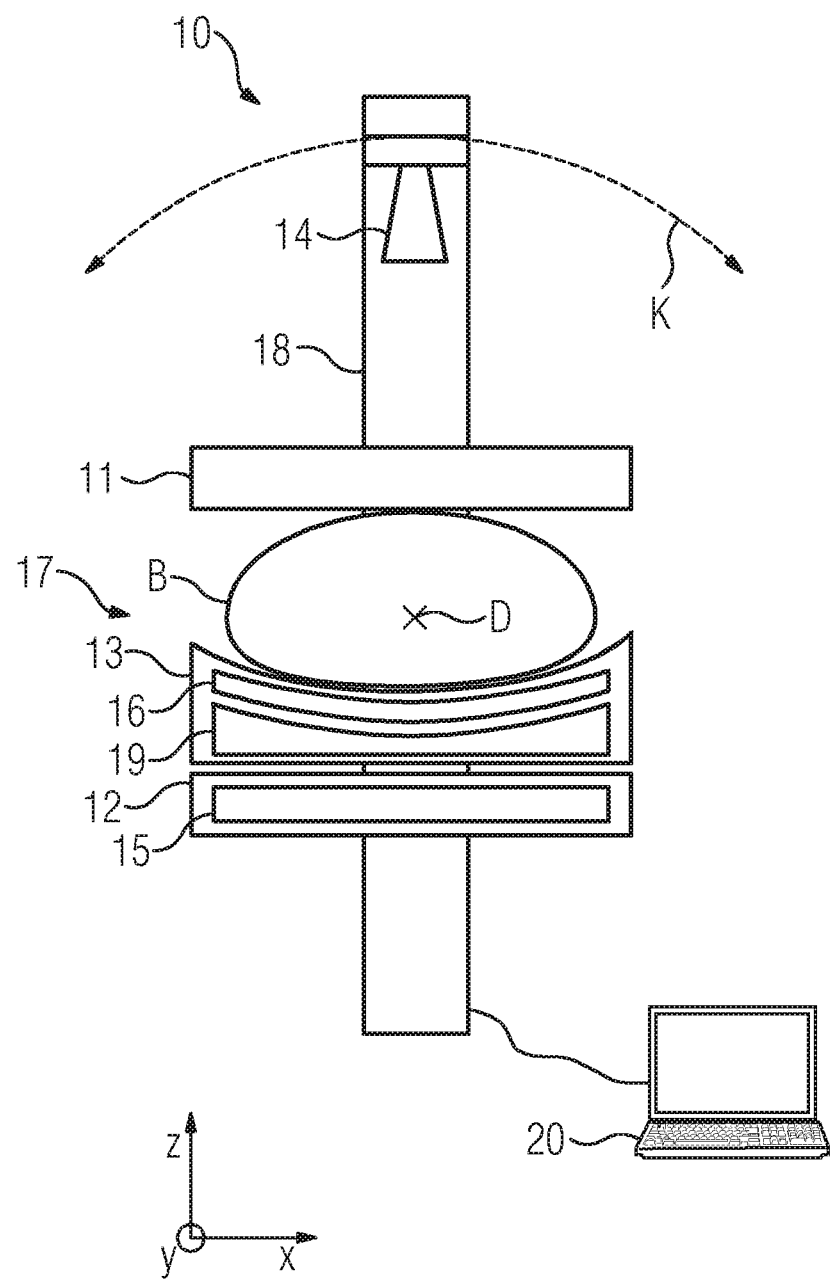
FIG. 2 shows a mammography installation in a second example embodiment.

FIG. 2 shows the mammography installation 10 in a frontal view in a second example embodiment, wherein the support device 13 and the integrated ultrasound transducer 16 are designed to be deformable such that they can be adapted to the breast B of the patient. The integrated ultrasound transducer 16 is arranged on an elastic substrate. In this example embodiment, the support device 13 with the integrated ultrasound transducer 16 is adapted to the breast B, whereby an acoustic coupling is improved in comparison with the example embodiment in FIG. 1.

The mammography installation 10 has a computing unit 20 and/or porcessor, wherein the mammography installation 10 is designed to determine a deformation of the integrated ultrasound transducer 16 and the computing unit 20 is designed to reconstruct an ultrasonic image data record in accordance with the deformation. The computing unit 20 has a monitor for displaying the radiographic image data record and the ultrasonic image data record.

The support device 13 has a cushion 19. The support device 13 has a first side facing the breast locating region 17 and a second side facing the compression device 12 at which the support device 13 is arranged, wherein the first side comprises the integrated ultrasound transducer 16. The second side comprises the cushion 19. The cushion 19 is therefore arranged between the second compression device 12 and the integrated ultrasound transducer 16.

The X-ray emitter 14 is so arranged as to be mobile in a circular arc K, said circular arc K being defined about a rotational axis D which is oriented perpendicular to the system axis of the mammography installation 10. In this case, the rotational axis D is parallel to the y-axis. The X-ray emitter 14 can travel through an angular range extending up to 90° along the circular arc K.

Figure 3:
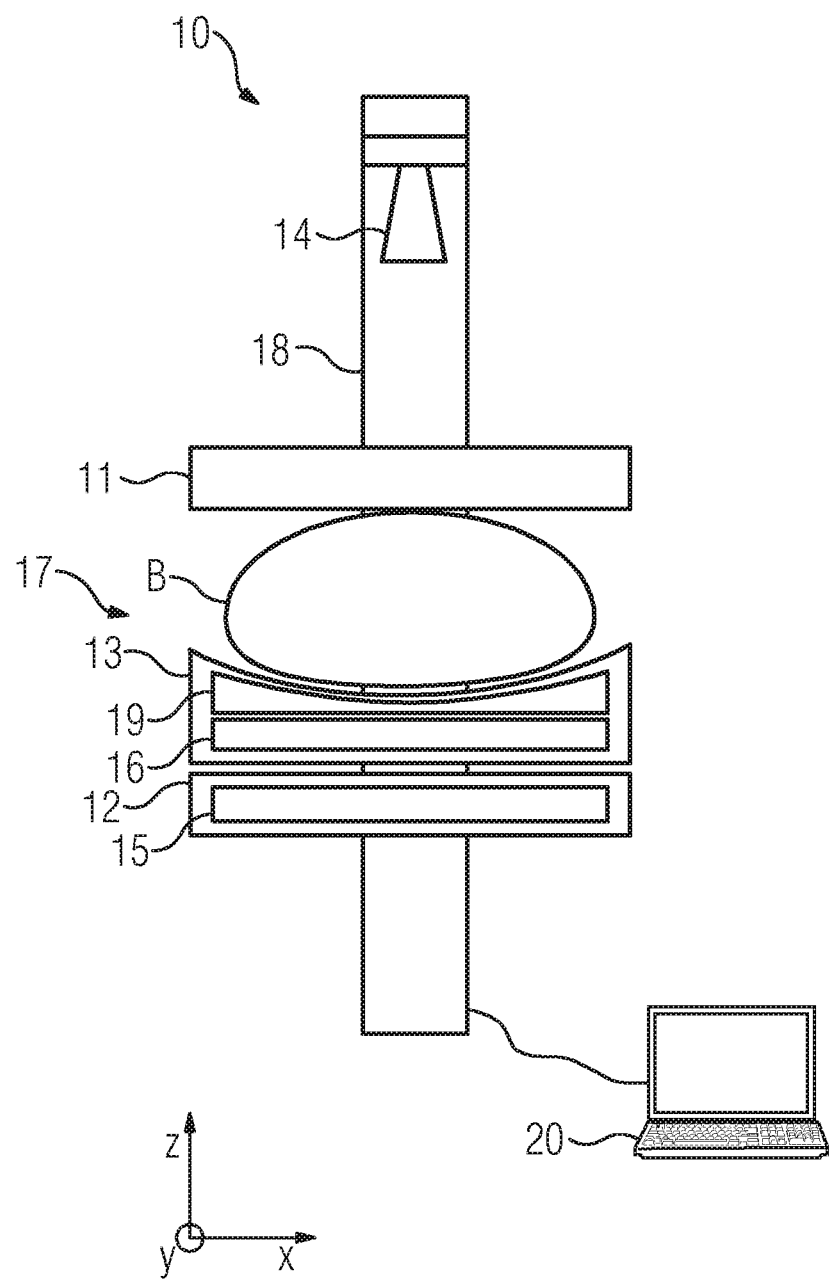
FIG. 3 shows a mammography installation in a third example embodiment.

In comparison with FIG. 1, the mammography installation 10 illustrated in FIG. 2 and in FIG. 3 is rotated by 90° about the system axis. FIG. 2 and FIG. 3 also show that the support device 13, in particular the integrated ultrasound transducer 16, is deformable along all spatial axes.

FIG. 3 shows the mammography installation 10 in a frontal view in a third example embodiment and in an alternative embodiment to FIG. 2. In this example embodiment, the second side of the support device 13 comprises the integrated ultrasound transducer 16. The first side of the support device 13 comprises the cushion 19. The cushion 19 is therefore arranged between the breast locating region 17 and the integrated ultrasound transducer 16. The support device 13 can typically be adapted to the breast B by virtue of the cushion 19. The cushion 19 is preferably designed as an ultrasound gel cushion or has comparable acoustic properties to an ultrasound gel cushion. This is advantageous in respect of the acoustic coupling in particular.

In this example embodiment, the support device 13 is adapted to the breast B, thereby improving the acoustic coupling in comparison with the example embodiment in FIG. 1.

The mammography installation 10 has the computing unit 20, wherein the integrated ultrasound transducer 16 is designed to capture a deformation of the support device 13 and the computing unit 20 is designed to reconstruct a radiographic image data record in accordance with the deformation the support device 13. The radiographic image data record and the ultrasonic image data record are displayed on the monitor of the computing unit 20.

Figure 4:
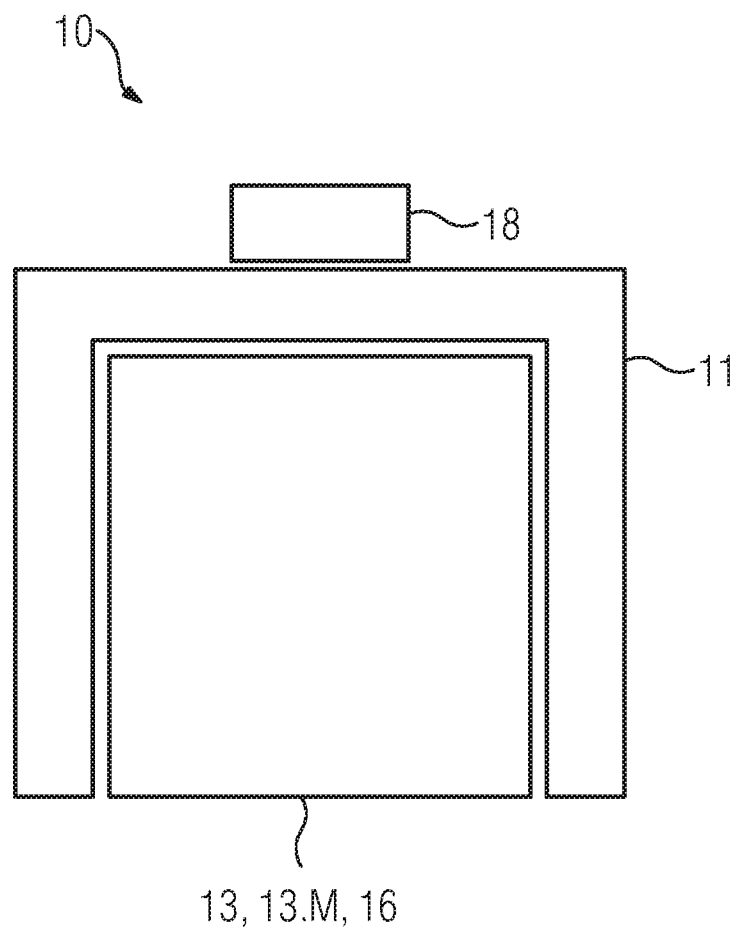
FIG. 4 shows a mammography installation in a fourth example embodiment.
Figure 4:
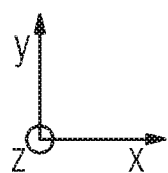

FIG. 4 shows a section of the mammography installation 10 from a bird's-eye view in a fourth example embodiment. In this example embodiment, the support device 13 is arranged at the first compression device 11. The support device 13 has a membrane 13.M, the integrated ultrasound transducer 16 being arranged at said membrane 13.M.

The supporting compression device, i.e. the first compression device 11 in this example embodiment, is designed as a frame. In this case, the frame is open on one side, i.e. the supporting compression device is designed to be C-shaped or U-shaped. The support device 13 and hence the integrated ultrasound transducer 16 are mounted or arranged within the frame.

FIG. 4 schematically shows the integrated ultrasound transducer 16 extending as an even layer in the x-y plane.

Figure 5:
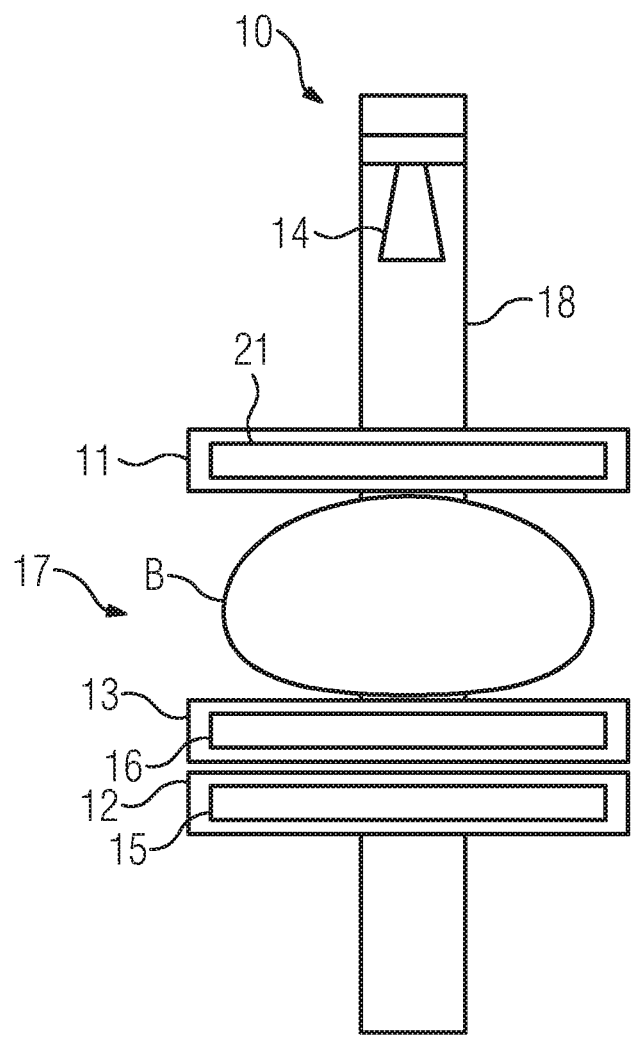
FIG. 5 shows a mammography installation in a fifth example embodiment.

FIG. 5 shows that the mammography installation 10 has a further ultrasound transducer 21 in addition to the integrated ultrasound transducer 16, said further ultrasound transducer 21 being arranged such that the breast locating region 17 is provided between the integrated ultrasound transducer 16 and the further ultrasound transducer 21. One of the two ultrasound transducers can preferably send and/or receive ultrasound waves in each case.

In this example embodiment, the further ultrasound transducer 21 is integrated in the first compression device 11. Alternatively, a further support device could comprise the further ultrasound transducer 21, said further support device being arranged at the first compression device 11. The explanations above in respect of the ultrasound transducer 16 also apply generally to the further ultrasound transducer 21, particularly the arrangement within a compression device which is designed as a frame.

Figure 6:
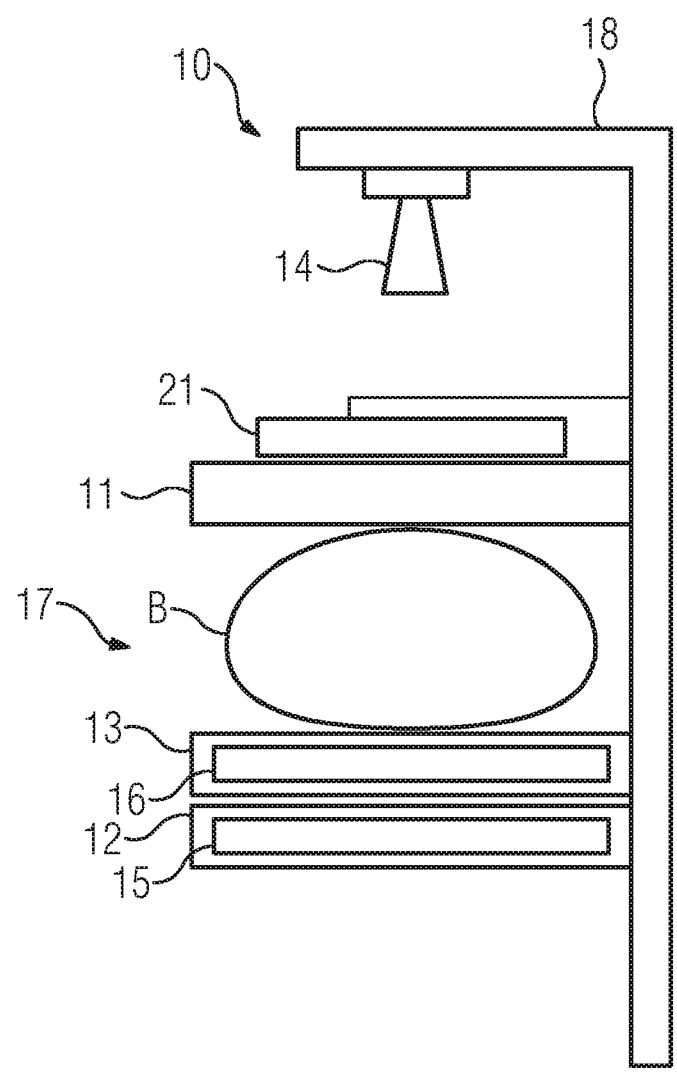
FIG. 6 shows a mammography installation in a sixth example embodiment.

FIG. 6 shows an alternative embodiment to that in FIG. 5. The further ultrasound transducer 21 is arranged between the X-ray emitter 14 and the first compression device 11 and is connected to the stand 18 by way of a further stand. It is conceivable in principle for the further ultrasound transducer 21 to be arranged outside a ray path during the radiographic imaging, said ray path being predetermined by the X-ray emitter 14 and the integrated X-ray detector 15, and moved into the ray path for the ultrasonic imaging.

Figure 7:
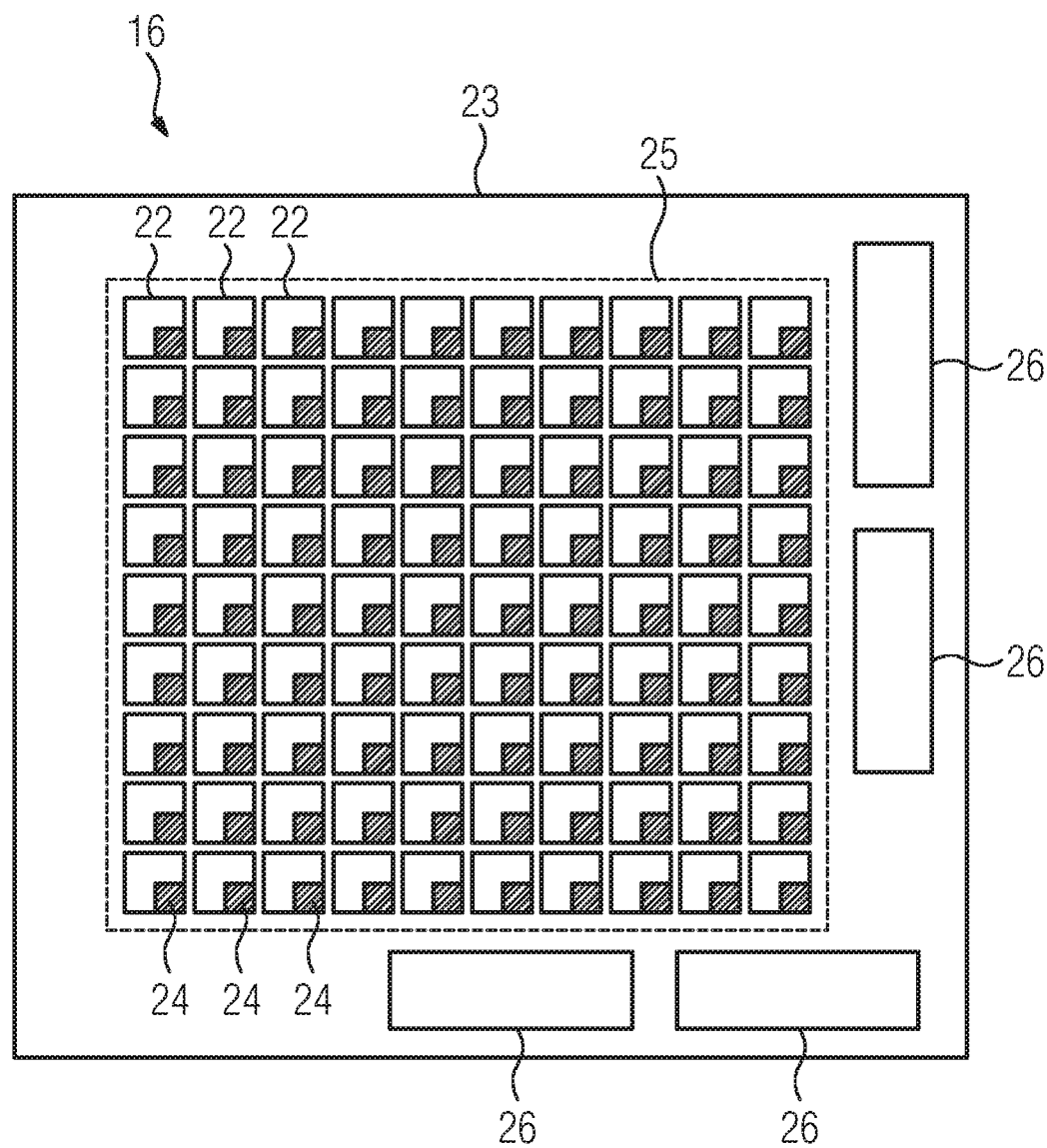
FIG. 7 shows a schematic view of the integrated ultrasound transducer 16 in a bird's-eye view.

FIG. 7 shows a schematic bird's-eye view of the integrated ultrasound transducer 16. The integrated ultrasound transducer 16 is based on pMUT technology. The ultrasound transducer elements 22 are arranged in the form of a matrix on a substrate 23 in the x-y plane and are distanced equally from each other. The substrate 23 may comprise a textile, glass, film, tissue and/or gauze. The substrate 23 can be elastic. In one case, the substrate 23 can correspond to the membrane 13.M of the support device 13. In another case, the substrate 23 is arranged at the support device 13 in addition to the membrane 13.M. Each ultrasound transducer element 22 corresponds to a pixel and has a control element 24 for activating the respective pixel. Each control element 24 preferably comprises a transistor. The substrate 23 has an exposed region 25 which encompasses the ultrasound transducer elements 22. An ultrasound transducer control unit 26, which is arranged outside the exposed region 25, is designed to activate the ultrasound transducer elements 22. Said activation can be effected individually or in groups. The ray path of the X-ray emitter 14 preferably covers exclusively the exposed region 25. In this case, the ultrasound transducer control unit 26, which is typically electronic and therefore potentially comprises X-ray-sensitive components, is excluded from the X-rays and is not irradiated.

Figure 8:
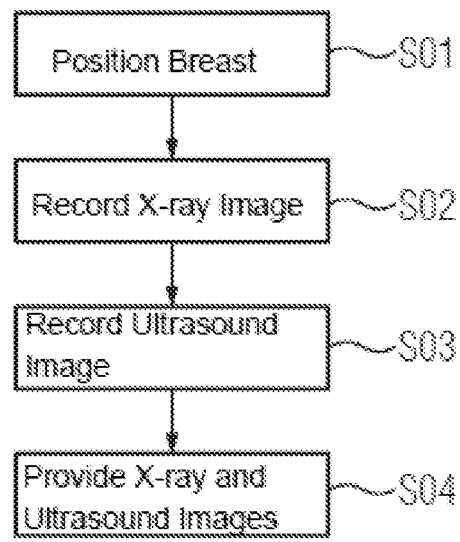
FIG. 8 shows a first flow diagram of the method.

FIG. 8 shows a first flow diagram of the method for providing a radiographic image data record and an ultrasonic image data record of a breast B of a patient via a mammography installation 10.

In this example embodiment, the radiographic image data record is captured before the ultrasonic image data record.

Method step S01 identifies the positioning of the breast B of the patient in a breast locating region 17 of the mammography installation 10.

Method step S02 identifies the capturing of the radiographic image data record of the breast B of the patient via an X-ray emitter 14 and an integrated X-ray detector 16 of the mammography installation 10.

Method step S03 identifies the capturing of the ultrasonic image data record of the breast B of the patient via an evenly spread integrated ultrasound transducer 16 of a support device 13 of the mammography installation 10, wherein the support device 13 holds the breast B of the patient steady between the capturing of the image data records.

Method step S04 identifies the provision of the radiographic image data record and the ultrasonic image data record.

Figure 9:
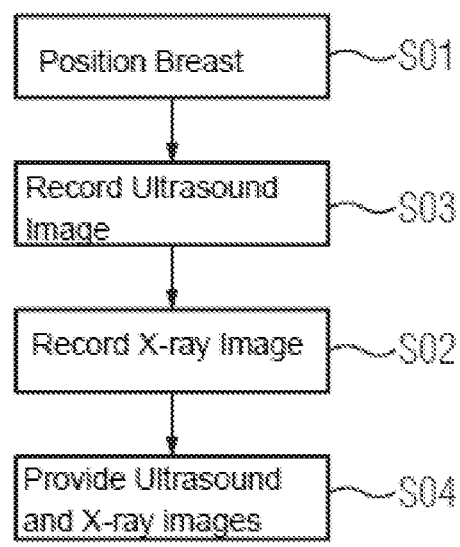
FIG. 9 shows a second flow diagram of the method.

FIG. 9 shows a second flow diagram of the method for providing a radiographic image data record and an ultrasonic image data record of a breast B of a patient via a mammography installation 10.

In this example embodiment, in comparison with the example embodiment in FIG. 8, the ultrasonic image data record is captured before the radiographic image data record. It is conceivable in principle for the ultrasonic image data record and the radiographic image data record to be captured quasi simultaneously.

Although the invention is illustrated and described in detail above with reference to the preferred example embodiments, the invention is not restricted to the examples disclosed herein and other variations may be derived therefrom without thereby departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A mammography installation for radiographic and ultrasonic imaging of a breast of a patient, comprising:
   a first compression device;
   a second compression device, including an integrated X-ray detector;
   an X-ray emitter;
   a support device between the first compression device and the second compression device and configured to contact a surface of the breast,
      wherein the suport device is arranged at the first compression device or at the second compression device, and including an integrated ultrasound transducer within the support device,
      wherein the integrated ultrasound transducer is designed as an even layer, and is arranged on an elastic substrate, and
      wherein the support device and the integrated ultrasound transducer are designed to be deformable and moldable so as to be adaptable to the breast of the patient; and
   a breast locating region, provided between the support device and one of the first compression device or the second compression device, the breast of the patient being positionable in the breast locating region, the integrated ultrasound transducer being oriented in a direction of the breast locating region.

2. The mammography installation of claim 1, further comprising:
   a processor, wherein the mammography installation is designed to determine a deformation of the integrated ultrasound transducer, and wherein the processor is configures to reconstruct an ultrasonic image data record in accordance with the deformation.

3. The mammography installation of claim 2, wherein the support device includes a membrane, and wherein the integrated ultrasound transducer is arranged at the membrane.

4. The mammography installation of claim 2, wherein the one of the first compression device and the second compression device, at which the support device is arranged, is designed as a frame, the support device being mounted within the frame.

5. The mammography installation of claim 2, wherein the support device includes a first side facing the breast locating region and a second side facing the one of the first compression device and the second compression device at which the support device is arranged, and wherein the integrated ultrasound transducer is located on the first side of the support device.

6. The mammography installation of claim 2, wherein the support device includes a first side facing the breast locating region, and a second side facing the one of the first compression device and the second compression device at which the support device is arranged, and wherein the second side of the support device includes the integrated ultrasound transducer.

7. The mammography installation of claim 1, wherein the support device includes a membrane, and wherein the integrated ultrasound transducer is arranged at the membrane.

8. The mammography installation of claim 1, wherein the one of the first compression device and the second compression device, at which the support device is arranged, is designed as a frame, the support device being mounted within the frame.

9. The mammography installation of claim 1, wherein the support device comprises a cushion.

10. The mammography installation of claim 1, wherein the support device includes a first side facing the breast locating region and a second side facing the one of the first compression device and the second compression device at which the support device is arranged, and wherein the integrated ultrasound transducer is located on the first side of the support device.

11. The mammography installation of claim 10, wherein the support device includes a cushion, and wherein the cushion is located on the second side of the support device.

12. The mammography installation of claim 10, wherein the support device includes a cushion, and wherein the cushion is located on the first side of the support device.

13. The mammography installation of claim 1, wherein the support device includes a first side facing the breast locating region, and a second side facing the one of the first compression device and the second compression device at which the support device is arranged, and wherein the second side of the support device includes the integrated ultrasound transducer.

14. The mammography installation of claim 13, wherein the support device includes a cushion, and wherein the cushion is located on the first side of the support device.

15. The mammography installation of claim 1, further comprising:
 a processor, wherein the integrated ultrasound transducer is designed to capture a deformation of the support device, and wherein the processor is configured to reconstruct a radiographic image data record in accordance with the deformation of the support device.

16. The mammography installation of claim 1, further comprising:
 a further ultrasound transducer, in addition to the integrated ultrasound transducer, wherein the further ultrasound transducer is arranged such that the breast locating region is providable between the integrated ultrasound transducer and the further ultrasound transducer.

\* \* \* \* \*